United States Patent
Ralph et al.

(10) Patent No.: US 7,122,055 B2
(45) Date of Patent: Oct. 17, 2006

(54) ARTIFICIAL INTERVERTEBRAL DISC HAVING A SPIDER SPRING FORCE RESTORING ELEMENT

(75) Inventors: James D. Ralph, Seaside Park, NJ (US); Stephen Tatar, Montville, NJ (US); Joseph P. Errico, Kirkland, WA (US)

(73) Assignee: SpineCore, Inc., Summit, NJ (US)

( * ) Notice: Subject to any disclaimer, the term of this patent is extended or adjusted under 35 U.S.C. 154(b) by 392 days.

(21) Appl. No.: 10/177,378

(22) Filed: Jun. 21, 2002

(65) Prior Publication Data

US 2003/0236571 A1    Dec. 25, 2003

(51) Int. Cl.
*A61F 2/44* (2006.01)
(52) U.S. Cl. ............... 623/17.14; 623/17.15
(58) Field of Classification Search ............ 623/17.11
See application file for complete search history.

(56) References Cited

U.S. PATENT DOCUMENTS

| | | | |
|---|---|---|---|
| 3,259,383 A * | 7/1966 | Johnson et al. ............ 267/161 |
| 5,458,642 A | 10/1995 | Beer et al. |
| 5,556,431 A | 9/1996 | Buttner-Janz |
| 5,562,738 A | 10/1996 | Boyd et al. |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,755,796 A | 5/1998 | Ibo et al. |
| 5,827,328 A | 10/1998 | Buttermann |
| 5,865,846 A | 2/1999 | Bryan et al. |
| 5,888,226 A | 3/1999 | Rogozinski |
| 5,895,428 A | 4/1999 | Berry |
| 5,899,941 A | 5/1999 | Nishijima |
| 5,989,291 A | 11/1999 | Ralph et al. |
| 6,001,130 A | 12/1999 | Bryan et al. |
| 6,019,792 A | 2/2000 | Cauthen |
| 6,039,763 A | 3/2000 | Shelokov |
| 6,063,121 A | 5/2000 | Xavier et al. |
| 6,113,637 A | 9/2000 | Gill et al. |
| 6,136,031 A | 10/2000 | Middleton |
| 6,146,421 A | 11/2000 | Gordon et al. |
| 6,156,067 A | 12/2000 | Bryan et al. |
| 6,179,874 B1 | 1/2001 | Cauthen |
| 6,228,118 B1 | 5/2001 | Gordon |

* cited by examiner

*Primary Examiner*—Thomas Barrett
(74) *Attorney, Agent, or Firm*—Lerner, David, Littenberg, Krumholz & Mentlik, LLP

(57) ABSTRACT

An artificial disc having a pair of opposing plates for seating against opposing vertebral bone surfaces, separated by a spider spring having a plurality of spring arms extending radially from a central hub. Various spring arm embodiments disclosed include spring arms that are straight, bowed, grooved, wavy, thinning, or thickening; and spring arms with parallel sides, radially outwardly diverging sides, or radially outwardly diverging and curving sides. Various spider spring embodiments disclosed include spider springs with central hubs that are solid, bored, have curvate sockets, or have semispherical protuberances. Various plate embodiments disclosed include plates having, on inwardly facing surfaces, a curvate socket, a semispherical protuberance, a circular recess, or a flat surface. The spider springs are disposable between the plates, through various disclosed couplings, so that the plates compress, rotate and angulate freely relative to one another, enabling the artificial disc to mimic a healthy natural intervertebral disc.

5 Claims, 9 Drawing Sheets

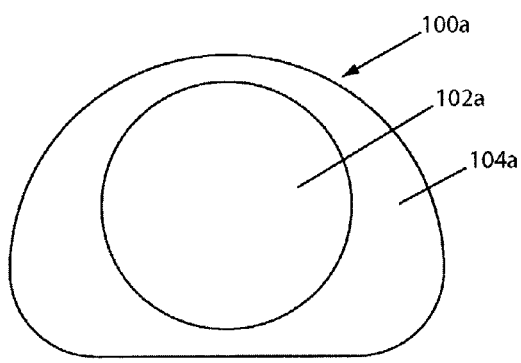
FIGURE 1.1
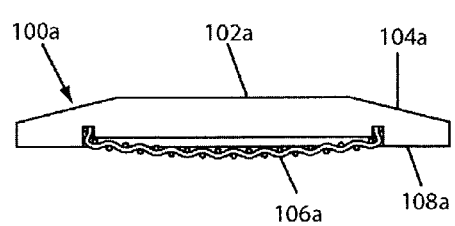
FIGURE 1.2
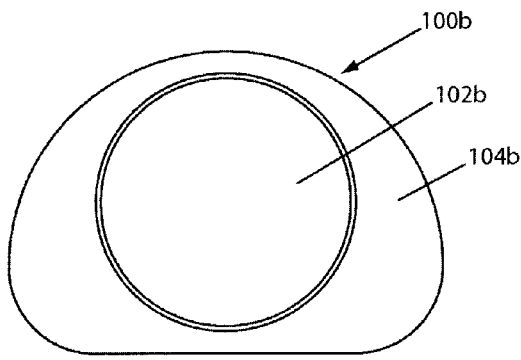
FIGURE 1.3
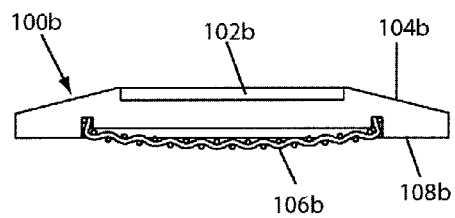
FIGURE 1.4

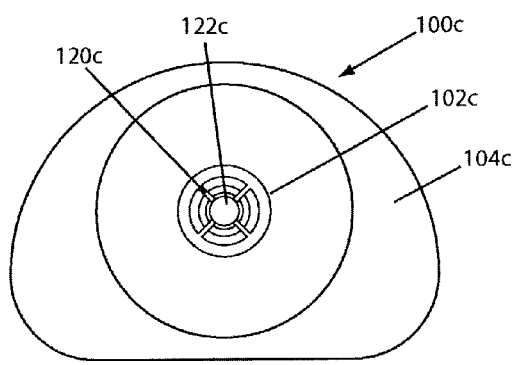
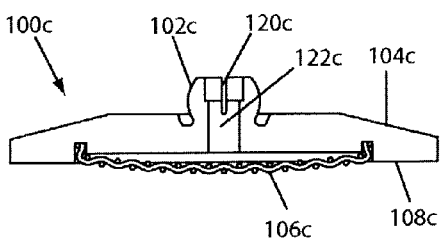
FIGURE 1.5      FIGURE 1.6
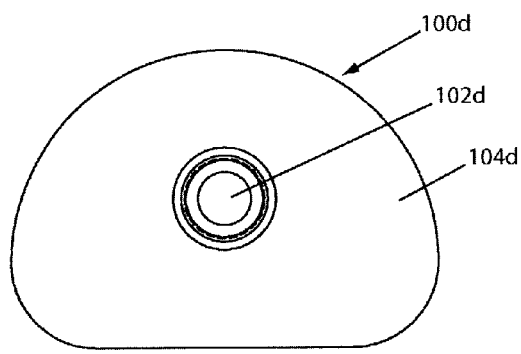
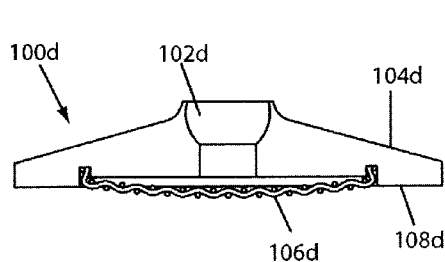
FIGURE 1.7      FIGURE 1.8
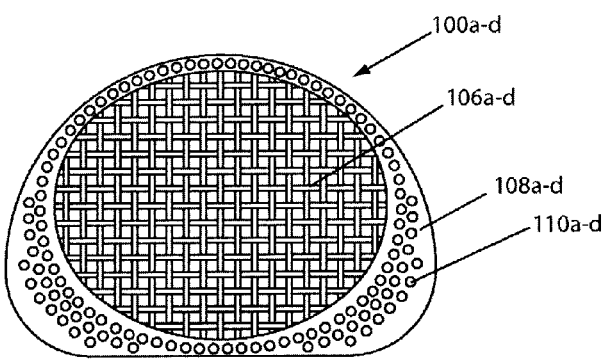
FIGURE 1.9

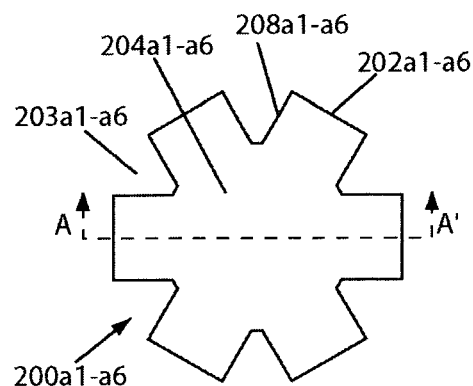
FIGURE 2.1
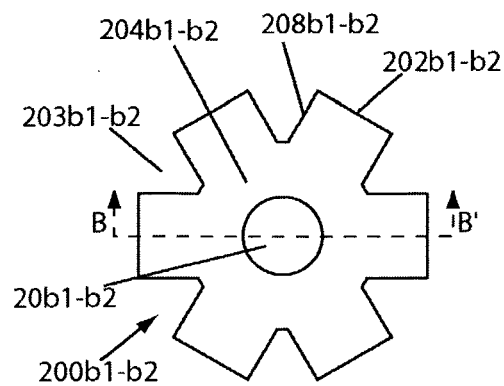
FIGURE 2.4
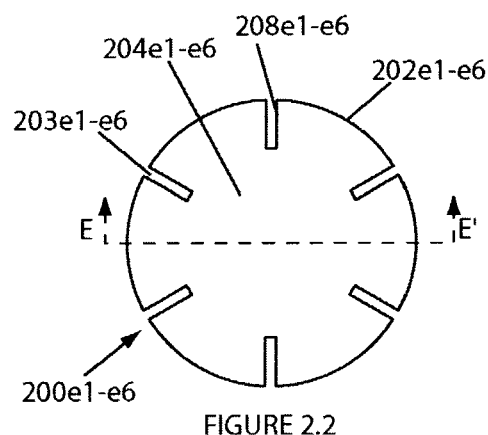
FIGURE 2.2
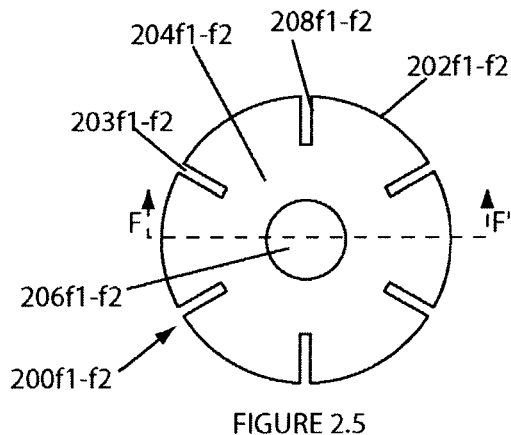
FIGURE 2.5
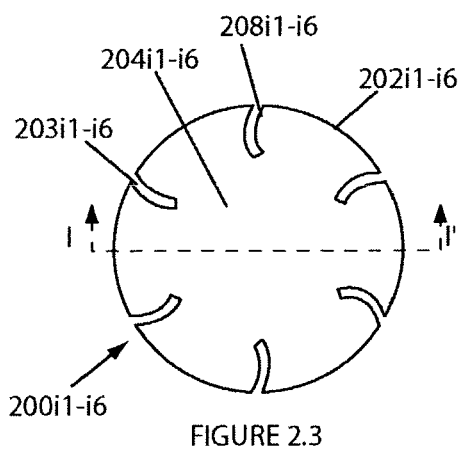
FIGURE 2.3
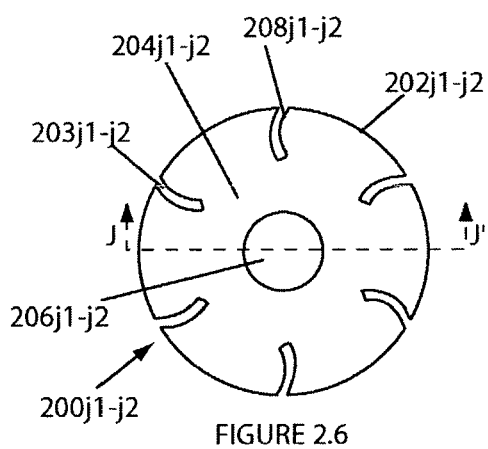
FIGURE 2.6

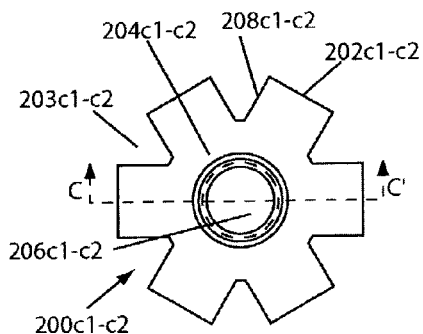
FIGURE 2.7
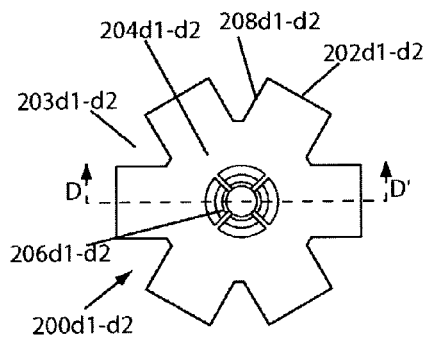
FIGURE 2.10
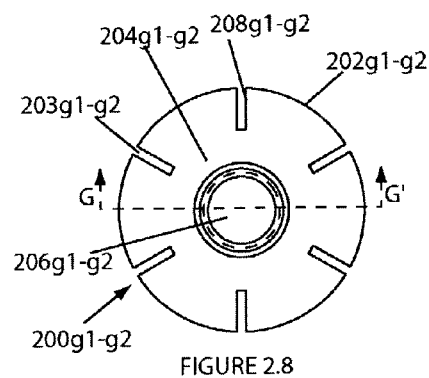
FIGURE 2.8
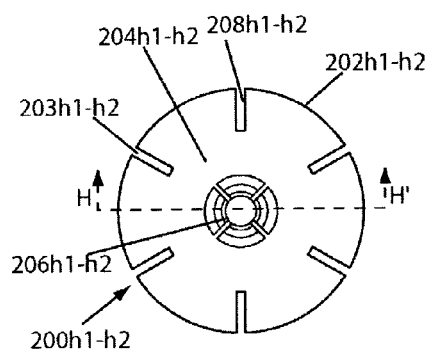
FIGURE 2.11
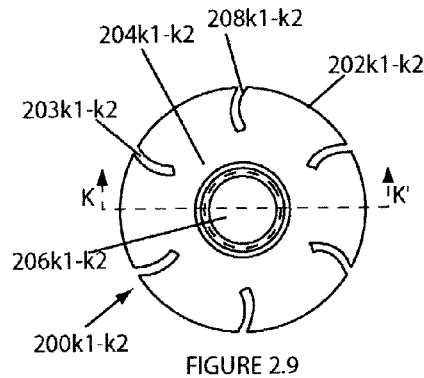
FIGURE 2.9
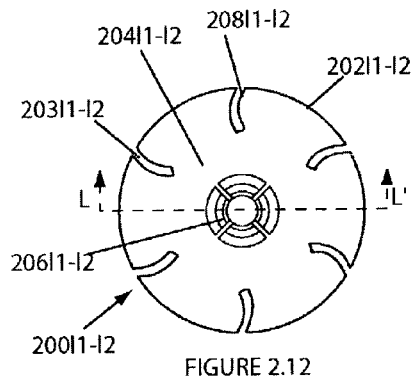
FIGURE 2.12

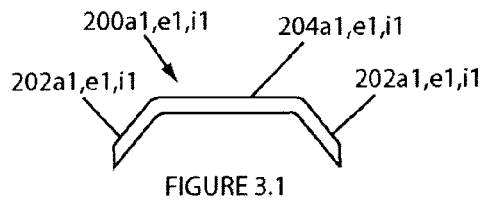
FIGURE 3.1
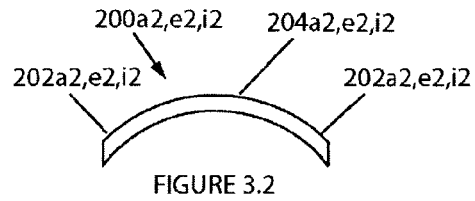
FIGURE 3.2
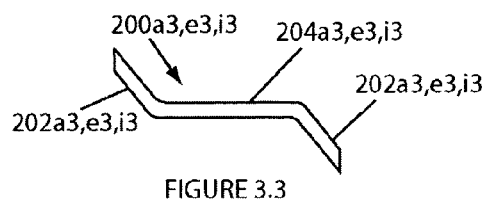
FIGURE 3.3
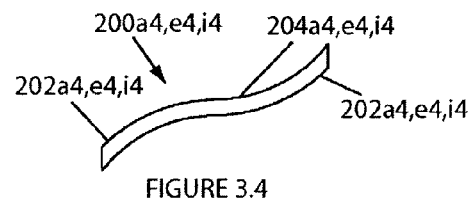
FIGURE 3.4
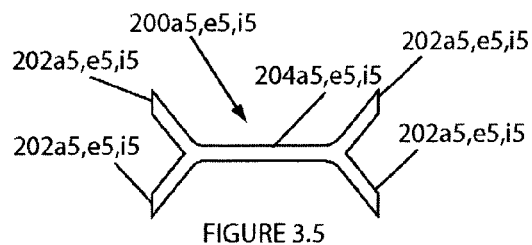
FIGURE 3.5
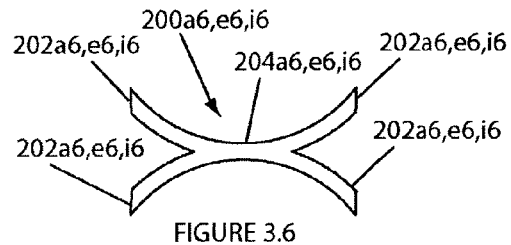
FIGURE 3.6
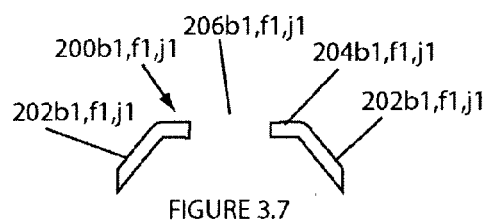
FIGURE 3.7
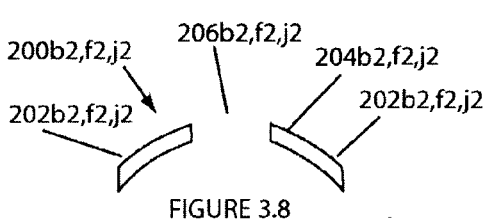
FIGURE 3.8
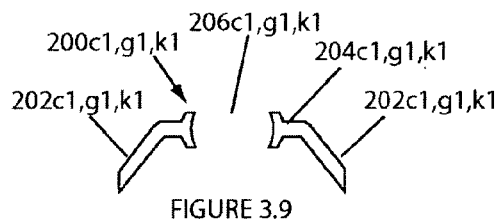
FIGURE 3.9
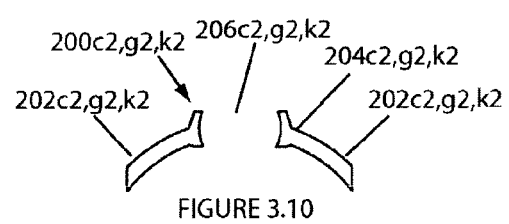
FIGURE 3.10
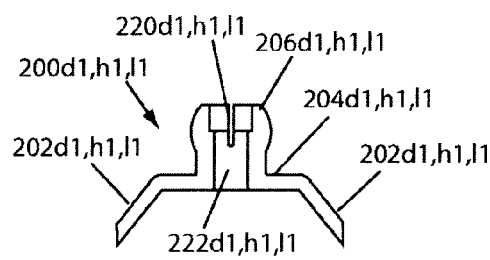
FIGURE 3.11
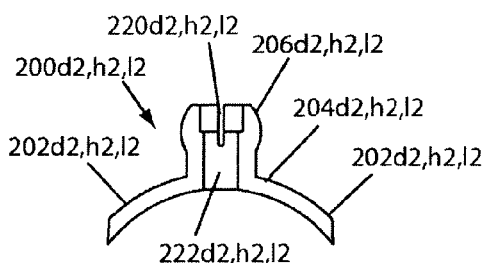
FIGURE 3.12

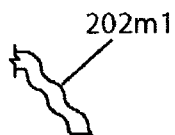
FIGURE 4.1
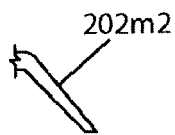
FIGURE 4.2
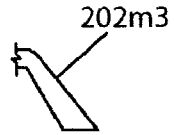
FIGURE 4.3
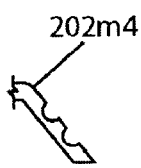
FIGURE 4.4
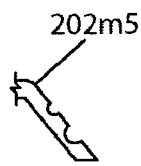
FIGURE 4.5
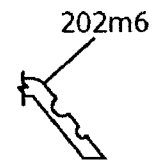
FIGURE 4.6
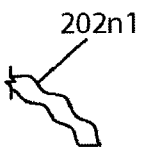
FIGURE 4.7
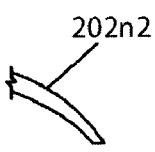
FIGURE 4.8
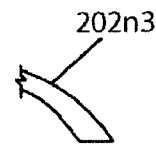
FIGURE 4.9
FIGURE 4.10
FIGURE 4.11
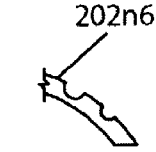
FIGURE 4.12
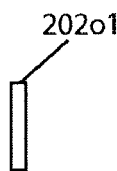
FIGURE 4.13
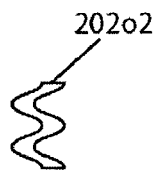
FIGURE 4.14
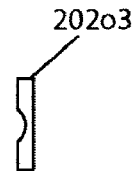
FIGURE 4.15
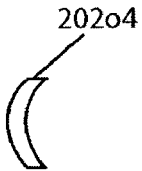
FIGURE 4.16
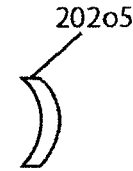
FIGURE 4.17
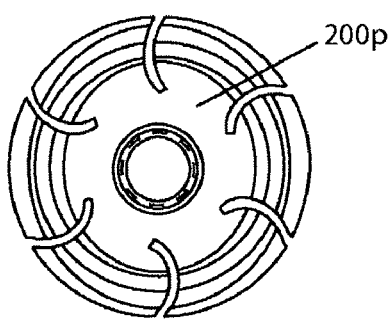
FIGURE 4.18
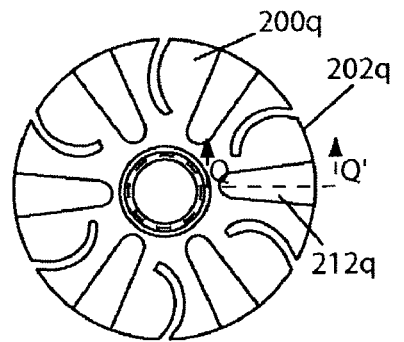
FIGURE 4.19
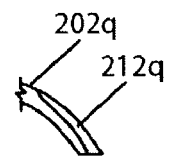
FIGURE 4.20

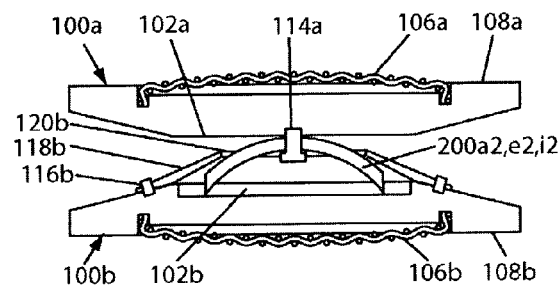
FIGURE 5.1
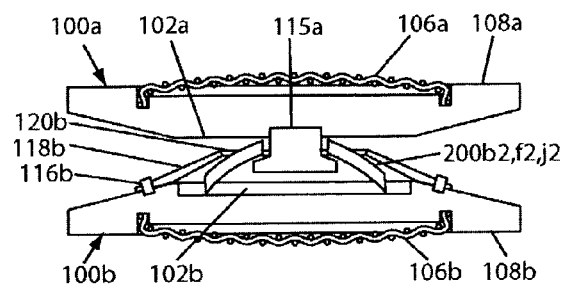
FIGURE 5.2
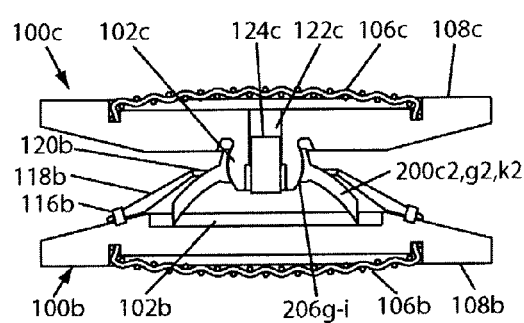
FIGURE 5.3
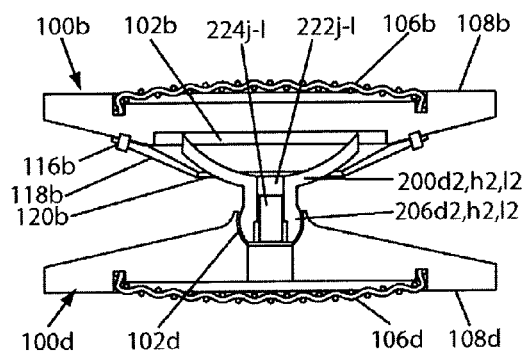
FIGURE 5.4

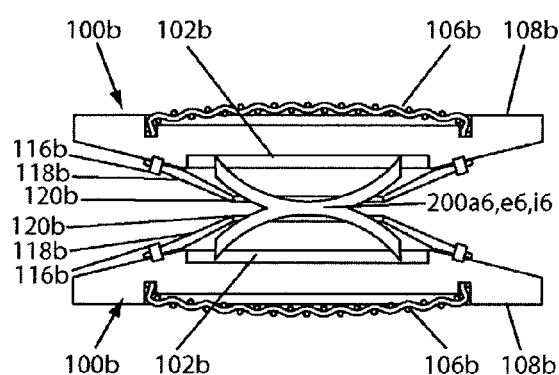
FIGURE 5.5
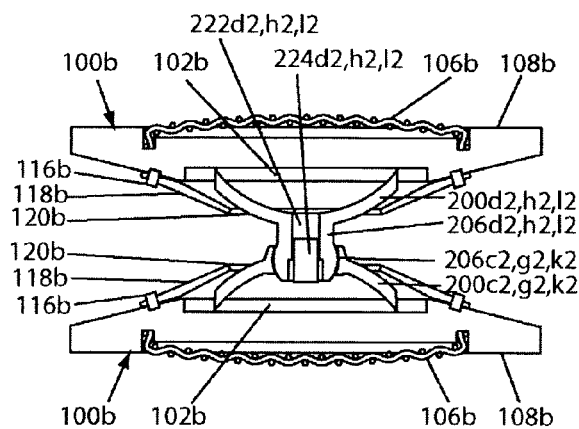
FIGURE 5.6
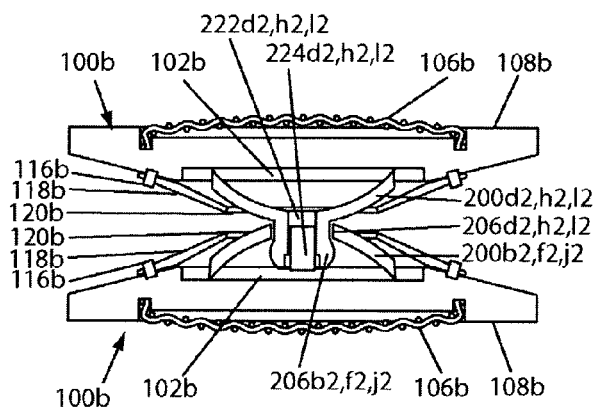
FIGURE 5.7
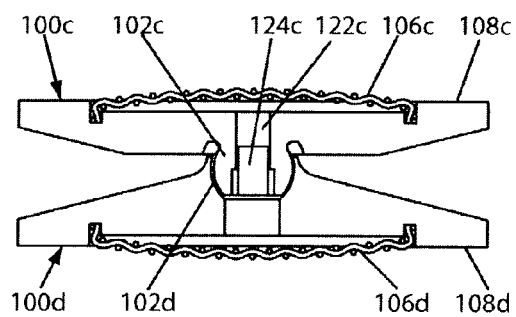
FIGURE 5.8

ARTIFICIAL INTERVERTEBRAL DISC HAVING A SPIDER SPRING FORCE RESTORING ELEMENT

FIELD OF THE INVENTION

This invention relates generally to a spinal implant assembly for implantation into the intervertebral space between adjacent vertebral bones to simultaneously provide stabilization and continued flexibility and proper anatomical motion, and more specifically to such a device that utilizes a spider spring force restoring element.

BACKGROUND OF THE INVENTION

The bones and connective tissue of an adult human spinal column consists of more than 20 discrete bones coupled sequentially to one another by a tri-joint complex that consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than 20 bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art that achieve immobilization and/or fusion of adjacent bones by implanting artificial assemblies in or on the spinal column. The region of the back that needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 6 and 7, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 7 the pair of cages 10 are inserted between the fifth lumbar vertebra (L5) and the top of the sacrum (S1)). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional materials, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the invention to provide an intervertebral spacer that stabilizes the spine without promoting a bone fusion across the intervertebral space.

It is further an object of the invention to provide an implant device that stabilizes the spine while still permitting normal motion.

It is further an object of the invention to provide a device for implantation into the intervertebral space that does not promote the abnormal distribution of biomechanical stresses on the patient's spine.

It is further an object of the invention to provide an artificial disc that has an plate attachment device (for attaching the plates of the artificial disc to the vertebral bones between which the disc is implanted) with superior gripping and holding strength upon initial implantation and thereafter.

It is further an object of the invention to provide an artificial disc plate attachment device that deflects during insertion of the artificial disc between vertebral bodies.

It is further an object of the invention to provide an artificial disc plate attachment device that conforms to the concave surface of a vertebral body.

It is further an object of the invention to provide an artificial disc plate attachment device that does not restrict the angle at which the artificial disc can be implanted.

It is further an object of the invention to provide an artificial disc that supports tension loads.

It is further an object of the invention to provide an artificial disc that provides a centroid of motion centrally located within the intervertebral space.

Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which is an artificial intervertebral disc or intervertebral spacer device comprising a pair of support members (e.g., spaced apart plates), each with an exterior surface. Because the artificial disc is to be positioned between the facing surfaces of adjacent vertebral bodies, the plates are arranged in a substantially parallel planar alignment (or slightly offset relative to one another in accordance with proper lordotic angulation) with the exterior surfaces facing away from one another. The plates are to mate with the vertebral bodies so as to not rotate relative thereto, but rather to permit the spinal segments to axially compress and bend relative to one another in manners that mimic the natural motion of the spinal segment. This natural motion is permitted by the performance of a spring disposed between the secured plates, and the securing of the plates to the vertebral bone is achieved through the use of a vertebral body contact element including, for example, a convex mesh attached to the exterior surface of each plate. Each convex mesh is secured at its perimeter, by laser welds, to the exterior surface of the respective plate. While domed in its initial undeflected conformation, the mesh deflects as necessary during insertion of the artificial disc between vertebral bodies, and, once the artificial disc is seated between the vertebral bodies, the mesh deforms as necessary under anatomical loads to reshape itself to the concave surface of the vertebral endplate. Thus, the wire mesh is deformably reshapeable under anatomical loads such that it conformably deflects against the concave surface to securably engage the vertebral body endplate. Stated alternatively, because the wire mesh is convexly shaped and is secured at its perimeter to the plate, the wire mesh is biased away from the plate but moveable toward the plate (under a load overcoming the bias; such a load is present, for example, as an anatomical load in the intervertebral space) so that it will securably engage the vertebral body endplate when disposed in the intervertebral space. This affords the plate having the mesh substantially superior gripping and holding strength upon initial implantation, as compared with other artificial disc products. The convex mesh further provides an osteoconductive surface through which the bone may ultimately grow. The mesh preferably is comprised of titanium, but can also be formed from other metals and/or non-metals. Inasmuch as the mesh is domed, it does not restrict the angle at which the artificial disc can be implanted. It should be understood that while the flexible dome is described herein preferably as a wire mesh, other meshed or solid flexible elements can also be used, including flexible elements comprises of non-metals and/or other metals. Further, the flexibility, deflectability and/or deformability need not be provided by a flexible material, but can additionally or alternatively be provided mechanically or by other means.

To enhance the securing of the plates to the vertebral bones, each plate further comprises at least a lateral porous ring (which may be, for example, a sprayed deposition layer, or an adhesive applied beaded metal layer, or another suitable porous coating known in the art). This porous ring permits the long-term ingrowth of vertebral bone into the plate, thus permanently securing the prosthesis within the intervertebral space. The porous layer may extend beneath the domed mesh as well, but is more importantly applied to the lateral rim of the exterior surface of the plate that seats directly against the vertebral body.

The spring disposed between the plates provides a strong restoring force when a compressive load is applied to the plates, and also permits rotation and angulation of the two plates relative to one another. While a wide variety of embodiments are contemplated, a preferred spring includes a spider spring utilized as the restoring force providing element. In general, a spider spring (due to its strength and structural stability) is highly suitable for use as a restoring force providing subassembly in an intervertebral spacer element that must endure considerable cyclical loading in an active human adult.

In particular, in order for the overall device to mimic the mechanical flexibility of the natural disc, it is desirable that the spring provide restoring forces that (1) are directed outward against the opposing plates, when a compressive load is applied to the plates; (2) that permit lateral bending and flexion and extension bending of the plates relative to parallel; (3) that do not permit lateral translation of the plates relative to one another during such bending; and (4) that do not substantially interfere with the rotation of the opposing plates relative to one another. The spider springs disclosed herein provide such functionality.

The spider spring of the invention has a plurality of spring arms extending radially and upwardly and/or downwardly from a central hub such that arm separation spaces are formed. The spring arms can be radially straight, where the height of the spider spring is linearly related to the radial length of the spring arm, or the spring arms can be radially bowed, where the height of the spider spring is not linearly related to the radial length of the spring arm (but rather the spider spring may, for example, be parabolic in shape). As a compressive load is applied to a spider spring, the forces are directed into a hoop stress that causes the spring arms to separate and move radially outwardly. This hoop stress is counterbalanced by the material strength of the spider spring, and the strain of the material causes a deflection in the height of the spider spring. Stated equivalently, a spider spring responds to a compressive load by deflecting compressively, but provides a restoring force that is proportional to the elastic modulus of the material in a hoop stressed condition. Thus, the restoring force of a spider spring is proportional to the elastic properties of the material from which it is made.

In addition, changing the configuration of the spring arms may modify the magnitude of the compressive load support and restoring force provided by the spider spring. Specifically, a variety of spring arms are illustrated and discussed herein. In some embodiments, the spring arms have radially parallel sides, forming radially widening arm separation spaces. In other embodiments, the spring arms have radially outwardly diverging sides, forming radially parallel arm separation spaces. In other embodiments, the spring arms have radially outwardly diverging and curving sides, forming curved arm separation spaces. The number and shape of the spring arms, and the formation of the resulting arm separation spaces, can be varied to accommodate desired applications, inasmuch as varying the dimensions will affect the behavior of the spider spring in expansion and retraction.

Additional configurations of the spring arms are possible, and are illustrated and discussed herein, to affect the behavior of the spider spring in expansion and retraction. In some embodiments, the spring arms extend radially downwardly from the central hub. In other embodiments, each spring arm is doubled, with a lower portion extending radially downwardly from the central hub and an upper portion extending radially upwardly from the central hub. It is possible to achieve a similar double spring arm configuration by mounting a balled spider spring to a bored spider spring to create a spring comprising opposing spider springs rotating and angulating with respect to one another about the resulting ball-and-bore joint at their narrow ends. It is also possible to achieve a similar double spring arm configuration by mounting a balled spider spring to a socketed spider spring to create a spring comprising opposing spider springs rotating and angulating with respect to one another about the resulting ball-and-socket joint at their narrow ends. In other embodiments, some spring arms extend radially downwardly from the central hub and other spring arms extend radially upwardly from the central hub. Preferably in these embodiments, the upwardly extending spring arms and the downwardly extending spring arms alternate.

Further configurations of the spring arms are possible, and are illustrated and discussed herein, to affect the behavior of the spider spring in expansion and retraction. In some embodiments, the spring arms have at least one concentric or radial characteristic that alters the performance of the spider spring in expansion and/or retraction. More specifically, in some embodiments, at least one spring arm is radially wavy. In other embodiments, at least one spring arm is radially thinning (the portion of the arm near the central hub is thicker than the portion of the arm near the outer edge of the arm). In other embodiments, at least one spring arm is radially thickening (the portion of the arm near the central hub is thinner than the portion of the arm near the outer edge of the arm). In other embodiments, at least one spring arm is concentrically grooved, having grooves that are similarly dimensioned to one another regardless of their relative radial distance from the central hub, or grooves that vary in dimension from one another depending on their relative radial distance from the central hub. In other embodiments, at least one spring arm is concentrically wavy. In other embodiments, at least one spring arm is radially grooved. In other embodiments, at least one spring arm is concentrically bowed, with the concave surface facing down. In other embodiments, at least one spring arm is concentrically bowed, with the concave surface facing up. It should be noted that with regard to spring arms having radial grooves, one or both of the depth and the width of each groove can be (1) decreasing along the length of the groove from the outer edge of the spring arm toward the central hub, (2) increasing along the length of the groove from the outer edge of the spring arm toward the central hub, (3) uniform along the length of the groove from the outer edge of the spring arm toward the central hub, or (4) varied along the length of each groove from the outer edge of the spring arm toward the central hub, either randomly or according to a pattern. It should be further noted that there is no lower or upper limit on the number of grooves contemplated by the invention.

For disposing the spider spring (whichever spider spring embodiment is chosen for the clinical application) between the plates, each spider spring embodiment has at least one feature suitable for this purpose, and the plates of the artificial disc comprise cooperating features suitable for this purpose. With regard to the spider spring coupling features, each spider spring embodiment has at least one wide end of the spider spring that expands and retracts as described above. Some spider spring embodiments have a solid central hub at a narrow end of the spider spring. Other spider spring embodiments have a bored central hub at a narrow end of the spider spring. Still other spider spring embodiments have a ball-shaped protuberance on a narrow end of the spider spring, similar to the ball-shaped protuberance described below with respect to the plate embodiments. Still other spider spring embodiments have a curvate socket on a narrow end of the spider spring, similar to the curvate socket described below with respect to the plate embodiments.

With regard to the structure and coupling features of the plates, four plate embodiments are illustrated and described herein, although other suitable plate embodiments can be used with the invention. Each of the four plate embodiments has the above described convex mesh on its outwardly facing surface, although other vertebral body attachment devices and mechanisms can be used without departing from the scope of the invention. Each of the four plate embodiments has a different inwardly facing surface from the other three plate embodiments. The first plate embodiment has a flat inwardly facing surface that accepts a fastener (e.g., rivet, plug, dowel, or screw; a rivet is used herein as an example) for securing a narrow end of a spider spring thereto, rotatably or otherwise. The second plate embodiment has a circular recess on its inwardly facing surface, for rotationally housing a wide end of a spider spring and allowing the wide end to expand in unrestricted fashion when the spider spring is compressed. The third plate embodiment has a semispherical (e.g., ball-shaped) protuberance on its inwardly facing surface, for rotatably and angulatably holding a narrow end of a spider spring, which narrow end includes a curvate socket having a substantially constant radius of curvature that is also substantially equivalent to the radius of the ball-shaped protuberance. The fourth plate embodiment has such a curvate socket on its inwardly facing surface, for rotatably and angulatably holding a narrow end of a spider spring, which narrow end includes a ball-shaped protuberance similar to that described above.

Each ball-shaped protuberance has an axial bore that receives a deflection preventing element (e.g., rivet, plug, dowel, or screw; a rivet is used herein as an example). Prior to the insertion of the rivet, the ball-shaped protuberance can deflect radially inward (so that the ball-shaped protuberance contracts). The insertion of the rivet eliminates the capacity for this deflection. The curvate socket, having a substantially constant radius of curvature that is also substantially equivalent to the radius of the ball-shaped protuberance, accommodates the ball-shaped protuberance for free rotation and angulation once the ball-shaped protuberance is disposed in the curvate socket, but in the ball-shaped protuberance's undeflected state, the ball-shaped protuberance cannot fit through the opening leading to the curvate socket. Therefore, the deflectability of the ball-shaped protuberance, prior to the insertion of the rivet, permits the ball-shaped protuberance to be inserted into the curvate socket. Subsequent introduction of the rivet into the axial bore of the ball-shaped protuberance prevents the ball-shaped protuberance from deflecting, and thus prevents the ball-shaped protuberance from escaping the socket. Thereby, the ball-shaped protuberance can be secured in the curvate socket so that it rotates and angulates therein through a range of angles, thus permitting the plates to rotate and angulate relative to one another through a corresponding range of angles equivalent to the fraction of normal human spine rotation and angulation (to mimic normal disc rotation and angulation).

With the four plate embodiments, the various spider spring embodiments, and the several manners in which they may be coupled together, it is possible to assemble a variety of artificial disc embodiments. Many examples are described herein, although many permutations that are contemplated and encompassed by the invention are not specifically identified herein, but are readily identifiable with an understanding of the invention as described. For example, all spider springs having a curvate socket can be coupled with a ball-shaped protuberance on either another spider spring or a plate. Also for example, all spider springs having a ball-shaped protuberance can be coupled with a curvate socket on either a spider spring or another plate, or with a bored central hub of a spider spring. Also for example, all plates having a curvate socket can be coupled with a ball-shaped protuberance on either another plate or a spider spring. Also for example, all plates having a ball-shaped protuberance can be coupled with a curvate socket on either another plate or a spider spring. Also for example, all spider springs without a ball-shaped protuberance or a curvate socket can be coupled with a flat inwardly facing surface of a plate. Also for example, each wide end of each spider spring can be coupled with a circular recess of a plate, and a shield can be secured over the spider spring after it has been placed in the circular recess to prevent the spider spring from escaping the recess when a tension load is applied to the plates.

Each assembly with a spider spring enjoys spring-like performance with respect to axial compressive loads, as well as long cycle life to mimic the axial biomechanical performance of the normal human intervertebral disc. The separate spring arms of the spider spring allow the spider spring to expand radially as the spring arms further separate under the compressive load, only to spring back into its undeflected shape when it is unloaded. As the spider spring compresses and decompresses, the walls of the circular recess of the second plate embodiment maintain the wide end of the spider spring within a prescribed boundary on the inwardly facing surface of the plate. The assemblies withstand tension loads on the outwardly facing surfaces, because (in embodiments having a spider spring) the shield retains the wide end in the circular recess and because (in embodiments having the ball-shaped protuberance) the rivet in the axial bore prevents the ball-shaped protuberance from deflecting, thus preventing it from exiting the curvate socket when the artificial disc is under a tension load and because (in embodiments in which the narrow end of a spider spring is secured by a rivet), the flanged portion of the rivet securing the narrow end of the spider spring prevents the spider spring from separating from the post portion of the rivet. Accordingly, once the plates are secured to the vertebral bones, the assembly will not come apart when a normally experienced tension load is applied to the spine, similar to the tension-bearing integrity of a healthy natural intervertebral disc.

Assemblies having the ball-and-socket joint also provide a centroid of motion centrally located within the intervertebral space, because the plates are made rotatable and angulatable relative to one another by the ball-shaped protuberance being rotatably and angulatably coupled in the curvate socket. The centroid of motion remains in the ball-shaped protuberance, and thus remains centrally located between the vertebral bodies, similar to the centroid of motion in a healthy natural intervertebral disc.

BRIEF DESCRIPTION OF THE DRAWINGS

FIGS. 1.1 through 1.9 show various embodiments of plates of the invention for use in an artificial disc of the invention.

FIGS. 1.1 and 1.2 show a bottom plan view and a side cutaway view, respectively, of a plate having a flat surface on its inwardly facing surface.

FIGS. 1.3 and 1.4 show a bottom plan view and a side cutaway view, respectively, of a plate having a circular recess on its inwardly facing surface.

FIGS. 1.5 and 1.6 show a bottom plan view and a side cutaway view, respectively, of a plate having a ball-shaped protuberance on its inwardly facing surface.

FIGS. 1.7 and 1.8 show a bottom plan view and a side cutaway view, respectively, of a plate having a curvate socket on its inwardly facing surface.

FIG. 1.9 shows a top plan view of any of the plates of FIGS. 1.1 through 1.8 (all appear the same from this view).

FIGS. 2.1 through 2.12 show top views of various embodiments of spider springs of the invention for use in an artificial disc of the invention, to illustrate a variety of spring arm configurations and central hub features contemplated by the invention.

FIG. 2.1 shows a spider spring having a solid central hub and spring arms with radially parallel sides.

FIG. 2.2 shows a spider spring having a solid central hub and spring arms with radially outwardly diverging sides.

FIG. 2.3 shows a spider spring having a solid central hub and spring arms with radially outwardly diverging and curving sides.

FIG. 2.4 shows a spider spring having a bored central hub and spring arms with radially parallel sides.

FIG. 2.5 shows a spider spring having a bored central hub and spring arms with radially outwardly diverging sides.

FIG. 2.6 shows a spider spring having a bored central hub and spring arms with radially outwardly diverging and curving sides.

FIG. 2.7 shows a spider spring having a central curvate socket and spring arms with radially parallel sides.

FIG. 2.8 shows a spider spring having a central curvate socket and spring arms with radially outwardly diverging sides.

FIG. 2.9 shows a spider spring having a central curvate socket and spring arms with radially outwardly diverging and curving sides.

FIG. 2.10 shows a spider spring having a central ball-shaped protuberance and spring arms with radially parallel sides.

FIG. 2.11 shows a spider spring having a central ball-shaped protuberance and spring arms with radially outwardly diverging sides.

FIG. 2.12 shows a spider spring having a central ball-shaped protuberance and spring arms with radially outwardly diverging and curving sides.

FIGS. 3.1 through 3.12 show side cross-section views of various embodiments of spider springs of the invention for use in an artificial disc of the invention, to illustrate additional varieties of spring arm configurations and central hub features of the invention.

FIG. 3.1 shows a spider spring having downwardly extending and radially straight spring arms.

FIG. 3.2 shows a spider spring having downwardly extending and radially bowed spring arms.

FIG. 3.3 shows a spider spring having radially straight spring arms, some of which are downwardly extending and some of which are upwardly extending.

FIG. 3.4 shows a spider spring having radially bowed spring arms, some of which are downwardly extending and some of which are upwardly extending.

FIG. 3.5 shows a spider spring having radially straight spring arms, each having a lower downwardly extending portion and an upper upwardly extending portion.

FIG. 3.6 shows a spider spring having radially bowed spring arms, each having a lower downwardly extending portion and an upper upwardly extending portion.

FIG. 3.7 shows a spider spring having downwardly extending and radially straight spring arms and a bored central hub.

FIG. 3.8 shows a spider spring having downwardly extending and radially bowed spring arms and a bored central hub.

FIG. 3.9 shows a spider spring having downwardly extending and radially straight spring arms and a central curvate socket.

FIG. 3.10 shows a spider spring having downwardly extending and radially bowed spring arms and a central curvate socket.

FIG. 3.11 shows a spider spring having downwardly extending and radially straight spring arms and a central ball-shaped protuberance.

FIG. 3.12 shows a spider spring having downwardly extending and radially bowed spring arms and a central ball-shaped protuberance.

FIGS. 4.1 through 4.20 show side cross-section views, end cross-section views, and top views of spring arms of various embodiments of spider springs, to illustrate additional varieties of spring arms of the invention.

FIG. 4.1 shows a straight spring arm that is radially wavy.

FIG. 4.2 shows a straight spring arm that is radially thinning.

FIG. 4.3 shows a straight spring arm that is radially thickening.

FIG. 4.4 shows a straight spring arm that is concentrically grooved, with grooves that are similarly dimensioned to one another regardless of their relative radial distance from the central hub.

FIG. 4.5 shows a straight spring arm that is concentrically grooved, with grooves that become smaller with a greater radial distance of the groove from the central hub.

FIG. 4.6 shows a straight spring arm that is concentrically grooved, with grooves that become larger with a greater radial distance of the groove from the central hub.

FIG. 4.7 shows a bowed spring arm that is radially wavy.

FIG. 4.8 shows a bowed spring arm that is radially thinning.

FIG. 4.9 shows a bowed spring arm that is radially thickening.

FIG. 4.10 shows a bowed spring arm that is concentrically grooved, with grooves that are similarly dimensioned to one another regardless of their relative radial distance from the central hub.

FIG. 4.11 shows a bowed spring arm that is concentrically grooved, with grooves that become smaller with a greater radial distance of the groove from the central hub.

FIG. 4.12 shows a bowed spring arm that is concentrically grooved, with grooves that become larger with a greater radial distance of the groove from the central hub.

FIG. 4.13 shows a spring arm having an extent that is concentrically straight.

FIG. 4.14 shows a spring arm having an extent that is concentrically wavy.

FIG. 4.15 shows a spring arm having an extent that is radially grooved.

FIG. 4.16 shows a spring arm having an extent that is concentrically bowed, with the concave surface facing down.

FIG. 4.17 shows a spring arm having an extent that is concentrically bowed, with the concave surface facing up.

FIG. 4.18 shows a spider spring having spring arms with concentric grooves having a concentrically varying width, wherein the concentric grooves collectively form two macro concentric grooves across all of the spring arms.

FIGS. 4.19 and 4.20 show a spider spring having at least one spring arm with a radial groove that varies in width and depth along the length of the groove.

FIGS. 5.1 through 5.8 show side views of various assembled artificial disc embodiments of the invention, with plates and shields of the invention in side cutaway view, but spider springs of the invention in side cross-section view.

FIG. 5.1 shows a spider spring having a solid central hub, with its central hub riveted to a flat surface of an upper plate and its wide end seated within a circular recess of a lower plate.

FIG. 5.2 shows a spider spring having a bored central hub, with its central hub rotatably secured by a flanged rivet to a flat surface of an upper plate and its wide end seated within a circular recess of a lower plate.

FIG. 5.3 shows a spider spring having a central curvate socket, with its curvate socket coupled to a ball-shaped protuberance of an upper plate and its wide end seated within a circular recess of a lower plate.

FIG. 5.4 shows a spider spring having a central ball-shaped protuberance, with its ball-shaped protuberance coupled to a curvate socket of an upper plate and its wide end seated within a circular recess of a lower plate.

FIG. 5.5 shows a spider spring having two wide ends, with its top wide end seated within a circular recess of an upper plate, and its bottom wide end seated within a circular recess of a lower plate.

FIG. 5.6 shows two spider springs, a bottom one having a central curvate socket and a top one having a central ball-shaped protuberance, with the curvate socket and the ball-shaped protuberance coupled together, and with the wide end of the top spider spring seated within a circular recess of an upper plate, and the wide end of the bottom spider spring seated within a circular recess of a lower plate.

FIG. 5.7 shows two spider springs, a bottom one having a bored central hub and a top one having a central ball-shaped protuberance, with the bored central hub and the ball-shaped protuberance coupled together, and with the wide end of the top spider spring seated within a circular recess of an upper plate, and the wide end of the bottom spider spring seated within a circular recess of a lower plate.

FIG. 5.8 shows a lower plate having a central curvate socket and an upper plate having a central ball-shaped protuberance, with the curvate socket and the ball-shaped protuberance coupled together.

DETAILED DESCRIPTION OF THE PREFERRED EMBODIMENTS

Figure 6:
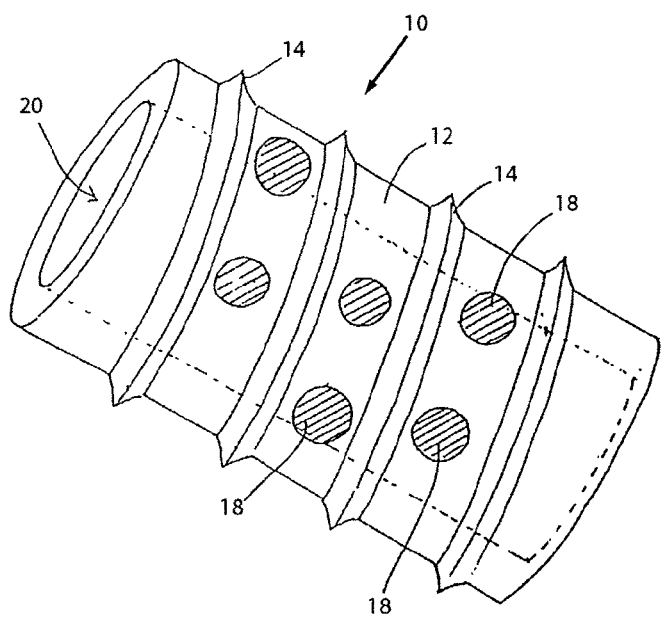
FIG. 6 shows a side perspective view of a prior art interbody fusion device.
Figure 7:
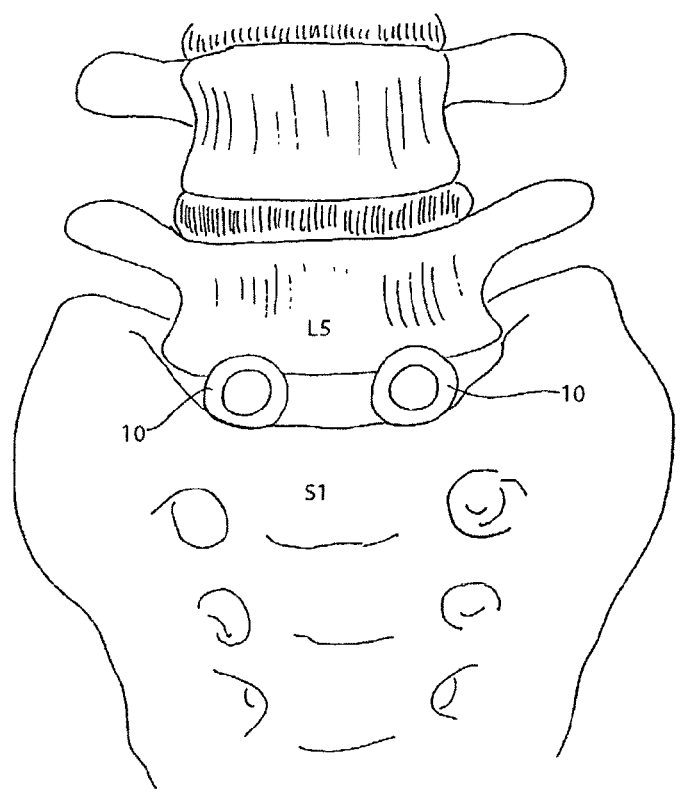
FIG. 7 shows a front view of the anterior portion of the lumbo-sacral region of a human spine, into which a pair of interbody fusion devices of FIG. 6 have been implanted.

While the invention will be described more fully hereinafter with reference to the accompanying drawings, in which particular embodiments and methods of implantation are shown, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

Referring now to FIGS. 1.1 through 1.9, various embodiments of plates of the invention for use in an artificial disc of the invention are shown in bottom plan views (FIGS. 1.1, 1.3, 1.5 and 1.7), side cutaway views (where cross-sectional areas and surfaces viewable behind them are shown) (FIGS. 1.2, 1.4, 1.6 and 1.8), and a top plan view (FIG. 1.9). More specifically, FIGS. 1.1 and 1.2 show a bottom plan view and a side cutaway view, respectively, of a first embodiment 100a of a plate. FIGS. 1.3 and 1.4 show a bottom plan view and a side cutaway view, respectively, of a second embodiment 100b of a plate. FIGS. 1.5 and 1.6 show a bottom plan view and a side cutaway view, respectively, of a third embodiment 100c of a plate. FIGS. 1.7 and 1.8 show a bottom plan view and a side cutaway view, respectively, of a fourth embodiment 100d of a plate. FIG. 1.9 shows a top plan view of any of the plates 100a–d (all appear the same from this view). As will be described in greater detail below, depending on the type of spider spring used in a particular embodiment of an artificial disc of the invention, two plates selected (for the manner in which they cooperate with the type of spider spring used in the embodiment) from these four embodiments will be used as opposing plates of the embodiment. Some embodiments of the artificial disc use two plates of the same plate embodiment.

Each plate 100a–d has an exterior surface 108a–d. Because the artificial disc of the invention is to be positioned between the facing surfaces of adjacent vertebral bodies, the two plates used in the artificial disc are disposed such that the exterior surfaces face away from one another (as best seen in FIGS. 5.1 through 5.8, discussed below). The two plates are to mate with the vertebral bodies so as to not rotate relative thereto, but rather to permit the spinal segments to axially compress and bend relative to one another in manners that mimic the natural motion of the spinal segment. This motion is permitted by the performance of a spider spring (described below) disposed between the secured plates. The mating of the plates to the vertebral bodies and the application of the spider spring to the plates are described below.

More particularly, each plate 100a–d is a flat plate (preferably made of a metal such as, for example, titanium) having an overall shape that conforms to the overall shape of the respective endplate of the vertebral body with which it is to mate. Further, each plate 100a–d comprises a vertebral body contact element (e.g., a convex mesh 106a–d) (preferably oval in shape) that is attached to the exterior surface 108a–d of the plate 100a–d to provide a vertebral body contact surface. The mesh 106a–d is secured at its perimeter, by laser welds, to the exterior surface 108a–d of the plate 100a–d. The mesh is domed in its initial undeflected conformation, but deflects as necessary during insertion of the artificial disc between vertebral bodies, and, once the artificial disc is seated between the vertebral bodies, deforms as necessary under anatomical loads to reshape itself to the concave surface of the vertebral endplate. This affords the plate having the mesh substantially superior gripping and holding strength upon initial implantation as compared with other artificial disc products. The mesh further provides an osteoconductive surface through which the bone may ultimately grow. The mesh is preferably comprised of titanium, but can also be formed from other metals and/or non-metals without departing from the scope of the invention.

Each plate 100a–d further comprises at least a lateral ring 110a–d that is osteoconductive, which may be, for example, a sprayed deposition layer, or an adhesive applied beaded metal layer, or another suitable porous coating. This porous ring permits the long-term ingrowth of vertebral bone into the plate, thus permanently securing the prosthesis within the intervertebral space. It shall be understood that this porous layer 110a–d may extend beneath the domed mesh 106a–d as well, but is more importantly applied to the lateral rim of the exterior surface 108a–d of the plate 100a–d that seats directly against the vertebral body.

It should be understood that the convex mesh attachment devices and methods described herein can be used not only with the artificial discs and artificial disc plates described or referred to herein, but also with other artificial discs and artificial disc plates, including, but not limited to, those currently known in the art. Therefore, the description of the mesh attachment devices and methods being used with the artificial discs and artificial disc plates described or referred to herein should not be construed as limiting the application and/or usefulness of the mesh attachment device.

With regard to the disposition of a spider spring between two plates, each of the plates 100a–d comprises features for applying the spider spring thereto, and the various application methods are described below. More specifically, the first plate embodiment 100a includes an inwardly facing surface 104a that includes a flat surface 102a that accepts a fastener (e.g., rivet, plug, dowel, or screw; a rivet 114a is used herein as an example) (shown in FIG. 5.1) for securing a narrow end of a spider spring thereto, rotatably or otherwise.

The second plate embodiment 100b includes an inwardly facing surface 104b that includes a circular recess 102b for rotationally housing a wide end of a spider spring and allowing the wide end to expand in unrestricted fashion when the spider spring is compressed, and the inwardly facing surface 104b also accepts fasteners (e.g., rivets, plugs, dowels, or screws; rivet 116b are used herein as examples) (shown in FIGS. 5.1 through 5.7) for securing a shield 118b (the purpose and application of the shield are described below and shown on FIGS. 5.1 through 5.7).

The third plate embodiment 100c includes an inwardly facing surface 104c that includes an inwardly directed semispherical (e.g., ball-shaped) protuberance 102c. The ball-shaped protuberance 102c includes a series of slots 120c that render the ball-shaped protuberance 102c radially compressible and expandable in correspondence with a radial pressure (or a radial component of a pressure applied thereto). The ball-shaped protuberance 102c further includes an axial bore 122c that accepts a deflection preventing element (e.g., rivet, plug, dowel, or screw; a rivet 124c is used herein as an example) (shown in FIGS. 5.3 and 5.8). (Alternatively, the axial bore can be threaded to accept a screw.) Prior to the insertion of the rivet 124c, the ball-shaped protuberance 102c can deflect radially inward because the slots 120c will narrow under a radial pressure. The insertion of the rivet 124c eliminates the capacity for this deflection. Therefore, the ball-shaped protuberance 102c, before receiving the rivet 124c, can be compressed to seat in a curvate socket portion of a spider spring and, once the ball-shaped protuberance 102c has been seated in the curvate socket, the rivet 124c can be inserted into the axial bore 122c to ensure that the ball-shaped protuberance 102c remains held in the curvate socket. A hole can be provided in the opposing plate so that the interior of the device may be readily accessed if a need should arise.

The fourth plate embodiment 100d includes an inwardly facing surface 104d that includes a central curvate socket 102d for receiving therein a ball-shaped protuberance of the type described above. Not only can the curvate socket 102d accept the ball-shaped protuberance 102c of the third plate embodiment 100c, but (as will be discussed below) the curvate socket 102d can accept a similar ball-shaped protuberance on a narrow end of a spider spring. Each curvate socket (whether on a plate or on a narrow end of a spider spring) has a substantially constant radius of curvature that is also substantially equivalent to the radius of the ball-shaped protuberance with which it mates, so that when the ball-shaped protuberance is secured therein, the ball-shaped protuberance can rotate and angulate freely relative to the curvate socket through a range of angles, thus permitting the opposing plates to rotate and angulate freely relative to one another through a corresponding range of angles equivalent to the fraction of normal human spine rotation and angulation (to mimic normal disc rotation and angulation).

Referring now to FIGS. 2.1 through 2.12, top views of various embodiments of spider springs of the invention for use in an artificial disc of the invention are shown to illustrate a variety of spring arm configurations and central hub features that are merely a subset of the spring arm configurations and central hub features contemplated by the invention. More specifically, each spider spring (e.g., 200a1–l2) has spring arms (e.g., 202a1–l2), with arm sides (e.g., 208a1–l2), extending radially from a central hub (e.g., 204a1–l2) such that arm separation spaces (e.g., 203a1–l2) are formed. In some embodiments (e.g., 200a1–d2), the spring arms (e.g., 202a1–d2) have radially parallel sides (e.g., 208a1–d2), forming radially widening arm separation spaces (e.g., 203a1–d2). In other embodiments (e.g., 200e1–h2), the spring arms (e.g., 202e1–h2) have radially outwardly diverging sides (e.g., 208e1–h2), forming radially parallel arm separation spaces (e.g., 203e1–h2). In other embodiments (e.g., 200i1–l2), the spring arms (e.g., 202i1–l2) have radially outwardly diverging and curving sides (e.g., 208i1–l2), forming curved arm separation spaces (e.g., 203i1–l2). The number and shape of the spring arms, and the formation of the resulting arm separation spaces, can be varied to accommodate any desired application, inasmuch as varying the dimensions will affect the expansion and retraction behavior of the spider spring.

Generally, as a compressive load is applied to a spider spring, the forces are directed into a hoop stress that causes the spring arms to move radially outwardly and the arms separation spaces to expand. This hoop stress is counterbalanced by the material strength of the spider spring, and the strain of the material causes a deflection in the height of the spider spring. Stated equivalently, a spider spring responds to a compressive load by deflecting compressively, but provides a restoring force that is proportional to the elastic modulus of the material in a hoop stressed condition. It should be understood that spider springs other than those shown are contemplated by the invention, including but not limited to spider springs having more or fewer arms, and including spider springs having arms configured differently than those shown (e.g., with radially outwardly converging sides), and including spider springs having at least two arms that are configured differently from one another.

With regard to the, central hub features shown on FIGS. 2.1 through 2.12, these are discussed in greater detail below with reference to FIGS. 5.1 through 5.7 regarding methods of applying the spider springs to the plates discussed above. However, for properly understanding the discussions of FIGS. 3.1 through 3.12 and 4.1 through 4.20, it is important to summarize here that some spider spring embodiments (e.g., 200a1–a6,e1–e6,i1–i6) have solid central hubs (e.g., 204a1–a6,e1–e6,i1–i6), other spider spring embodiments (e.g., 200b1–b2,f1–f2,j1–j2) have on their central hubs (e.g., 204b1–b2,f1–f2,j1–j2) a bore (e.g., 206b1–b2,f1–f2,j1–j2), still other spider spring embodiments (e.g., 200c1–c2,g1–g2, k1–k2) have on their central hubs (e.g., 204c1–c2,g1–g2, k1–k2) curvate sockets (e.g., 206c1–c2,g1–g2,k1–k2) similar to those described as being on plate embodiment l00d, and still other spider spring embodiments (e.g., 200d1–d2, h1–h2,l1–l2) have on their central hubs (e.g., 204d1–d2, h1–h2,l1–l2) ball-shaped protuberances (e.g., 206d1–d2, h1–h2,l1–l2) similar to those described as being on plate embodiment 100c.

Referring now also to FIGS. 3.1 through 3.12, side cross-section views (where only the cross-sectional area is shown) of various embodiments of spider springs are shown to illustrate additional varieties of spring arm configurations and central hub features that are merely a subset of the spring arm configurations and central hub features contemplated by the invention. The side cross-sections are taken along cut lines A–A', B–B', C–C', D–D', E–E', F–F', G–G', H–H', I–I', J–J', K–K', and L-L' on FIGS. 2.1 through 2.12, as applicable. It should be understood that a single side cross-section view can illustrate more than one spider spring embodiment, given that some spider springs look similar from a top view but not similar from a side cross-section view. For example, FIGS. 3.1 through 3.6 illustrate spider spring embodiments that from a top view appear as any of FIGS. 2.1 through 2.3. Also, for example, FIGS. 3.7 and 3.8 illustrate spider spring embodiments that from a top view appear as any of FIGS. 2.4 through 2.6. Also, for example, FIGS. 3.9 and 3.10 illustrate spider spring embodiments that from a top view appear as any of FIGS. 2.7 through 2.9. And, for example, FIGS. 3.11 and 3.12 illustrate spider spring embodiments that from a top view appear as any of FIGS. 2.10 through 2.12. Multiple reference numbers for elements in FIGS. 3.1 through 3.12 are used to identify these multiple permutation possibilities. Stated alternatively, each of FIGS. 3.1 through 3.12 is not a side cross-section view that is associated with only one of the top views of FIGS. 2.1 through 2.12, but rather is associatable with more than one of the top views of FIGS. 2.1 through 2.12.

More specifically, FIGS. 3.1, 3.3, 3.5, 3.7, 3.9, and 3.11 show configurations where the extents of the spring arms (e.g., 202a1,e1,i1, a3,e3,i3, a5,e5,i5, b1,f1,j1, c1,g1,k1, d1,h1,l1) are radially straight, such that the height of the spider spring (e.g., 200a1,e1,i1, a3,e3,i3, a5,e5,i5, b1,f1,j1, c1,g1,k1, d1,h1,l1) is linearly related to the radial length of the spring arms. FIGS. 3.2, 3.4, 3.6, 3.8, 3.10, and 3.12 show configurations where the extents of the spring arms (e.g., 202a2,e2,i2, a4,e4,i4, a6,e6,i6, b2,f2,j2, c2,g2,k2, d2,h2,l2) are radially bowed, such that the height of the spider spring (e.g., 200a2,e2,i2, a4,e4,i4, a6,e6,i6,b2,f2,j2, c2,g2,k2, d2,h2,l2) is not linearly related to the radial length of the spring arms (but rather the spider spring may, for example, be parabolic in shape). FIGS. 3.1, 3.2, and 3.7 through 3.12 show configurations in which the spring arms (e.g., 202a1–a2,b1–e2,f1–i2,j1–l2) extend radially downwardly from the central hub (e.g., 204a1–a2,b1–e2,f1–i2,j1–l2). FIGS. 3.5 and 3.6 show configurations in which the spring arms (e.g., 202a5–a6,e5–e6,e5–e6,i5–i6) are doubled, with lower portions extending radially downwardly from the central hub (e.g., 204a5–a6,e5–e6,i5–i6) and upper portions extending radially upwardly from the central hub. As will be discussed below, it is possible to achieve a similar double spring arm configuration by mounting a balled spider spring (e.g., 200d1–d2,h1–h2,l1–l2) to a bored spider spring (e.g., 200b1–b2,f1–f2,j1–j2) to create a spring comprising opposing spider springs rotating and angulating with respect to one another about the resulting ball-and-bore joint at their narrow ends. Further, as will be discussed below, it is also possible to achieve a similar double spring arm configuration by mounting a balled spider spring (e.g., 200d1–d2, h1–h2,l1–l2) to a socketed spider spring (e.g., 200c1–c2, g1–g2,k1–k2) to create a spring comprising opposing spider springs rotating and angulating with respect to one another about the resulting ball-and-socket joint at their narrow ends. FIGS. 3.3 and 3.4 show configurations in which some of the spring arms (e.g., 202a3–a4,e3–e4,i3–i4) extend radially downwardly from the central hub (e.g., 204a3–a4, $e3$–$e4$,$i3$–$i4$) and others of the spring arms extend radially upwardly from the central hub. Preferably, as in the configurations shown in FIGS. 3.3 and 3.4, the upwardly extending spring arms and the downwardly extending spring arms alternate.

Further with regard to the central hub features shown in top views on FIGS. 2.1 through 2.12, these are shown in side cross-section views in FIGS. 3.1 through 3.12. More specifically, the solid central hubs (e.g., 204$a1$–$a6$,$e1$–$e6$,$i1$–$i6$) are shown in FIGS. 3.1 through 3.6. The bored central hubs (e.g., 204$b1$–$b2$,$f1$–$f2$,$j1$–$j2$) are shown in FIGS. 3.7 and 3.8. The curvate sockets (e.g., 206$c1$–$c2$,$g1$–$g2$,$k1$–$k2$) are shown in FIGS. 3.9 and 3.10. The ball-shaped protuberances (e.g., 206$d1$–$d2$,$h1$–$h2$,$l1$–$l2$) are shown in FIGS. 3.11 and 3.12. It should be understood that the specific dimensions of the ball-shaped protuberance, the mechanism for radial compressibility of the ball-shaped protuberance, and the mechanism for preventing radial compression of the ball-shaped protuberance are not limited to those shown, but rather can be varied and changed without departing from the scope of the invention.

Referring now also to FIGS. 4.1 through 4.12, side cross-section views (where only the cross-sectional area is shown) of spring arms (e.g., 202$m1$–$n6$) of various embodiments of spider springs are shown to illustrate additional varieties of spring arm configurations that are merely a subset of the spring arm configurations contemplated by the invention. The side cross-sections are taken from the base of the spring arm (i.e., the portion that connects with the central hub) radially to the outermost edge of the spring arm. It should be understood that with regard to the remaining structure of the spider springs having the illustrated circumferential extents, the spider springs can share all or some of the features (e.g., spring arm configurations, arm side configurations, arm separation space configurations, number of spring arms, direction of spring arms, central hub configurations, etc.) of the other spider spring embodiments discussed herein, and/or have features that are different and/or configured differently.

More specifically, FIGS. 4.1 through 4.12 show configurations where the extents of the spring arms are generally radially straight (FIGS. 4.1 through 4.6), such that the height of the spider spring is linearly related to the radial length of the spring arms, or generally radially bowed (FIGS. 4.7 through 4.12), such that the height of the spider spring is not linearly related to the radial length of the spring arms, but additionally have at least one concentric or radial characteristic that alters the performance of the spider spring in expansion and/or retraction. For example, the spring arms in FIGS. 4.1 and 4.7 are radially wavy. Also for example, the spring arms in FIGS. 4.2 and 4.8 are radially thinning (the portion of the arm near the central hub is thicker than the portion of the arm near the outer edge of the arm). Also for example, the spring arms in FIGS. 4.3 and 4.9 are radially thickening (the portion of the arm near the central hub is thinner than the portion of the arm near the outer edge of the arm). Also for example, the spring arms in FIGS. 4.4, 4.5, 4.6, 4.10, 4.11 and 4.12 are concentrically grooved, having grooves that are similarly dimensioned to one another regardless of their relative radial distance from the central hub (FIGS. 4.4 and 4.10), or grooves that vary in dimension from one another depending on their relative radial distance from the central hub (FIGS. 4.5, 4.6, 4.11 and 4.12). For example, the width and depth of the grooves in FIG. 4.5 and the grooves in FIG. 4.11 become smaller with the greater radial distance of the groove from the central hub. And, for example, the width and depth of the grooves in FIG. 4.6 and the grooves in FIG. 4.12 become larger with the greater radial distance of the groove from the central hub.

In some spring arm embodiments, at least one dimension of a concentric groove (such as, for example, the width and/or depth) can be applied to vary concentrically across the spring arm. Further, in some embodiments, the concentric grooves can be applied to the spring arms of a spider spring embodiment in a macro pattern, where the concentric grooves on each individual arm extend from one arm to another to form one or more macro concentric grooves, each of which extends across all or some of the spring arms. FIG. 4.18 shows one example of a configuration where two macro concentric grooves, each concentrically varying in width, are applied to the spring arms of a spider spring embodiment 200$p$.

Referring now also to FIGS. 4.13 through 4.17, end cross-section views (where only the cross-sectional area is shown) of spring arms (e.g., 202$o1$–$o5$) of various embodiments of spider springs are shown to illustrate additional varieties of spring arm configurations that are merely a subset of spring arm configurations contemplated by the invention. The end cross-sections are taken from one side of the spring arm to the other (i.e., perpendicular to the side cross-sections discussed above with regard to FIGS. 4.1 through 4.12). It should be understood that with regard to the remaining structure of the spider springs having the illustrated circumferential extents, the spider springs can share all or some of the features (e.g., spring arm configurations, arm side configurations, arm separation space configurations, number of spring arms, direction of spring arms, central hub configurations, etc.) of the other spider spring embodiments discussed herein, and/or have features that are different and/or configured differently.

More specifically, FIG. 13 shows a spring arm configuration where the extent of the arm is concentrically uniform, whereas FIGS. 4.14 through 4.17 show spring arm configurations where the extents of the spring arms have at least one concentric or radial characteristic that alters the performance of the spider spring in expansion and/or retraction, as compared to the spring arm configuration of FIG. 13. For example, the spring arm in FIG. 4.14 is concentrically wavy. The spring arm in FIG. 4.15 is radially grooved. The spring arm in FIG. 4.16 is radially bowed, with the concave surface facing down. The spring arm in FIG. 4.17 is radially bowed, with the concave surface facing up.

It should be noted that with regard to spring arms having at least one radial groove (e.g., FIG. 4.15), one or both of the depth and the width of each groove can be (1) decreasing along the length of the groove from the outer edge of the spring arm toward the central hub, (2) increasing along the length of the groove from the outer edge of the spring arm toward the central hub, (3) uniform along the length of the groove from the outer edge of the spring arm toward the central hub, or (4) varied along the length of each groove from the outer edge of the spring arm toward the central hub, either randomly or according to a pattern. A spider spring embodiment 200$q$ having a spring arm 202$q$ with a radially grooved configuration, as an example of case (1), is shown in top view in FIG. 4.19 and in spring arm side cross-section view in FIG. 4.20 (taken along cut lines Q-Q' in FIG. 4.19), where both the width and depth of a groove 212$q$ vary along the length of the groove. Moreover, it can be the case that each groove is not formed similarly to one or more other grooves (on the same spring arm or other spring arms), but rather one or more grooves are formed in any of the above-mentioned fashions, while one or more other grooves are formed in another of the above-mentioned fashions or other fashions. It should be clear that any groove pattern can be implemented without departing from the scope of the invention.

It should be understood that the spring arms contemplated by the invention include, but are not limited to, those having only one concentric or radial characteristic at a time. The use of more than one concentric or radial characteristic per arm is contemplated, as well as the use of concentric and radial characteristics simultaneously. Further, it is contemplated that some spider spring embodiments will use only radially straight arms, some spider spring embodiments will use only radially bowed arms, and some spider spring embodiments that will use both radially straight arms as well as radially bowed arms.

Referring again to FIGS. 2.1 through 2.12, each of the spider springs is suitable for disposition between two opposing plates of the invention. As noted above, and as discussed in greater detail below, depending on the type of spider spring used in the particular embodiment of the artificial disc of the invention, the two plates are selected (for the manner in which they cooperate with the type of spider spring used in the embodiment) from the four plate embodiments, for use as opposing plates of the embodiment. Some embodiments of the artificial disc use two plates of the same plate embodiment. In each embodiment, the plates are made rotatable and angulatable relative to one another (to mimic the functionality of a healthy natural intervertebral disc) by having a spring member, and/or by the manner in which the spring member is secured to one or more of the plates, and/or by the manner in which two spring members are secured to one another, or by the manner in which the plates are secured to one another. Further in each embodiment, the same couplings, and/or through the use of additional coupling elements (e.g., shields and/or rivets and/or screws), enable the artificial disc embodiments to withstand tension loading (to mimic the functionality of a healthy natural intervertebral disc). Further in embodiments having a spring member, the spring member enables the artificial disc embodiments to axially compress and axially restore (to mimic the functionality of a healthy natural intervertebral disc).

Referring now also to FIGS. 5.1 through 5.8, these figures show side views of various assembled artificial disc embodiments contemplated by the invention. The side views show the plates in side cutaway view, but the spider springs in side cross-section view. It should be understood that the illustrated embodiments do not encompass all embodiments contemplated by the invention, but rather were selected for illustration purposes to show how the features of the various illustrated plate embodiments cooperate with corresponding features of the various illustrated spider spring embodiments, when the spider springs are disposed between opposing plates of the invention. While only certain assembled artificial disc embodiments are shown, it should be understood that spider springs not shown but having like plate coupling features can be secured to cooperating plates in the manner illustrated, in various permutations and combinations, and the same have been withheld from illustration for purposes of conciseness and clarity only to avoid duplicative illustration that would only visually reiterate that which can be understood from the descriptions herein.

For example, and referring to FIG. 5.1, some spider springs (e.g., spider springs $200a1-a2,e1-e2,i1-i2$) are designed to have the narrow end of the spider spring secured to a flat surface on an inwardly facing surface of a plate (e.g., the flat surface $102a$ on the inwardly facing surface $104a$ of plate $100a$), preferably those spider springs in which all of the spring arms extend downwardly or in which all of the spring arms extend upwardly (for both see, e.g., FIGS. 3.1 and 3.2 for side cross-section views of exemplary embodiments), both in contrast to having some spring arms extending downwardly and others extending upwardly (see, e.g., FIGS. 3.3 through 3.6). These spider springs preferably have a solid central hub (e.g., $204a1-a2,e1-e2,i1-i2$) that can be secured against the flat surface of the plate, e.g., by a fastener (e.g., rivet, plug, dowel, or screw; a rivet $114a$ is used herein as an example) (shown in FIG. 5.1). (If a screw is used, a threaded bore can be provided in the plate for its acceptance.) The rivet $114a$ prevents rotation of the spider spring relative to the plate against which it is secured, but as also discussed below with regard to the securing of the wide end of the spider spring, the plates are rotatable relative to one another because the wide end of the spider spring can rotate with respect to the plate having the circular recess in which the wide end seats (discussed below). Further, the plates are angulatable relative to one another because the spring arms of the spider spring can individually compress and restore, enabling one side of the spider spring to compress and restore as the plates angulate relative to one another, while other portions of the spider spring do not.

For example, and referring to FIG. 5.2, other spider springs (e.g., spider springs $200b1-b2,f1-f2,j1-j2$) are designed to have the narrow end of the spider spring rotatably secured to a flat surface on an inwardly facing surface of a plate (e.g., the flat surface $102a$ on the inwardly facing surface $104a$ of plate $100a$). These spider springs preferably have a central hub (e.g., $204b1-b2,f1-f2,j1-j2$) with a bore (e.g., $206b1-b2,f1-f2,j1-j2$) through which a flanged fastener (e.g., rivet, plug, dowel, or screw; a flanged rivet $115a$ is used herein as an example) (shown in FIG. 5.2) can be passed and secured to the flat surface of the plate. The flanged rivet $115a$ has a flanged portion at the end of a post portion. The post portion has a diameter smaller than the diameter of the bore, and a length that is longer than the thickness of the spider spring's central hub, and the flanged portion has a diameter greater than the diameter of the bore. Therefore, upon application of the rivet $115a$, the spider spring is secured to the plate so that it can still rotate with respect to the plate. (If a similarly flanged screw is used, a threaded bore can be provided in the plate for its acceptance.) As also discussed below with regard to the securing of the wide end of the spider spring, the plates are secondarily rotatable relative to one another because the wide end of the spider spring can rotate with respect to the plate having the circular recess in which the wide end seats (discussed below). Further, the plates are angulatable relative to one another because the spring arms of the spider spring can individually compress and restore, enabling one side of the spider spring to compress and restore as the plates angulate relative to one another, while other portions of the spider spring do not.

For another example, and referring to FIG. 5.3, other spider springs (e.g., spider springs $200c1-c2,g1-g2,k1-k2$) are designed to have the narrow end cooperate with a semispherical (e.g., ball-shaped) protuberance on an inwardly facing surface of a plate (e.g., the ball-shaped protuberance $102c$ on the inwardly facing surface $104c$ of plate $100c$). These spider springs preferably have a central hub (e.g., $204c1-c2,g1-g2,k1-k2$) with a curvate socket (e.g., $206c1-c2,g1-g2,k1-k2$) within which the ball-shaped protuberance is securable for free rotation and angulation through a range of angles. The structure of the curvate socket and the coupling of the ball-shaped protuberance with the curvate socket are as described above with regard to the curvate socket $102d$ on plate $10d$ and the ball-shaped protuberance 102c on plate 100c. As noted above, a deflection preventing element (e.g., rivet, plug, dowel, or screw; a rivet 124c is used herein as an example) applied to the axial bore 122c after the ball-shaped protuberance 102c has been inserted into the curvate socket prevents the deflection of the ball-shaped protuberance 102c so that it does not escape the curvate socket. The plates are rotatable relative to one another primarily because the ball-shaped protuberance rotates freely within the curvate socket, and secondarily because the wide end of the spider spring can rotate with respect to the plate having the circular recess in which the wide end seats (discussed below). Also, the plates are angulatable relative to one another primarily because the ball-shaped protuberance angulates freely within the curvate socket, and secondarily because the spring arms of the spider spring can individually compress and restore, enabling one side of the spider spring to compress and restore as the plates angulate relative to one another, while other portions of the spider spring do not.

For another example, and referring to FIG. 5.4, other spider springs (e.g., spider springs 200d1–d2,h1–h2,l1–l2) are designed to have the narrow end cooperate with a curvate socket on an inwardly facing surface of a plate (e.g., the central curvate socket 102d on plate 100d). These spider springs preferably have a central hub (e.g., 204d1–d2,h1–h2, l1–l2) with a semispherical (e.g., ball-shaped) protuberance (e.g., 206d1–d2,h1–h2,l1–l2) that is securable within the curvate socket for free rotation and angulation through a range of angles. The structure of the ball-shaped protuberance and the coupling of the ball-shaped protuberance with the curvate socket are as described above with regard to the curvate socket 102d on plate 100d and the ball-shaped protuberance 102c on plate 100c. Similar to rivet 124c discussed above, a deflection preventing element (e.g., a rivet, plug, dowel, or screw; rivets 224d1–d2,h1–h2,l1–l2 are used herein as examples) applied to the axial bore (e.g., 222d1–d2,h1–h2,l1–l2) after the ball-shaped protuberance (e.g., 206d1–d2,h1–h2,l1–l2) has been inserted into the curvate socket 102d prevents the deflection of the ball-shaped protuberance so that it does not escape the curvate socket. The plates are rotatable relative to one another primarily because the ball-shaped protuberance rotates freely within the curvate socket, and secondarily because the wide end of the spider spring can rotate with respect to the plate having the circular recess in which the wide end seats (discussed below). Also, the plates are angulatable relative to one another primarily because the ball-shaped protuberance angulates freely within the curvate socket, and secondarily because the spring arms of the spider spring can individually compress and restore, enabling one side of the spider spring to compress and restore as the plates angulate relative to one another, while other portions of the spider spring do not.

For another example, and referring to FIGS. 5.1 through 5.7, each of the spider springs is to have the wide end of the spider spring seat within a circular recess on an inwardly facing surface of a plate (e.g., the circular recess 102b on an inwardly facing surface 104b of plate 100b). More specifically, the wide end of the spider spring (e.g., 200a1–l2) fits within the circular recess 102b with room to expand when the spider spring (e.g., 200a1–l2) is under compression. Because the diameter of the circular recess is greater than the diameter of the wide end of the spider spring, unrestrained rotation of the spider spring relative to the plate is enabled, and compressive loading of the artificial disc (and therefore the spider spring) results in an unrestrained radial deflection of the spider spring, both as necessary for proper anatomical response. To prevent removal of the wide end of the spider spring from the circular recess when the artificial disc is loaded in tension, a shield 118b can be placed over the spider spring and secured by fasteners (e.g., rivets, plugs, dowels, or screws; rivets 116b are used herein as examples). The shield 118b can have a central hole 120b through which the curvate socket and the ball-shaped protuberance can pass (where applicable depending on the particular spider spring used) to accommodate efficient assembly of the artificial disc. The shield 118b can alternatively or additionally be formed from multiple shield parts, which would be useful, for example, in embodiments where no part of the spider member can pass through the central hole (see, e.g., the embodiment of FIG. 5.4, discussed below).

For another example, and referring to FIG. 5.5, some spider springs (e.g., spider springs 200a5–a6,e5–e6,i5–i6) are disposable between plates having the circular recess (e.g., plates of plate embodiment 100b), preferably those embodiments in which the spring arms are doubled, with a lower set extending radially downwardly from the central hub and an upper set extending radially upwardly from the central hub (see, e.g., FIGS. 3.5 and 3.6 for side cross-section views of exemplary embodiments) or in which some spring arms extend radially downwardly from the central hub and other spring arms extend radially upwardly from the central hub (see, e.g., FIGS. 3.3 and 3.4 for side cross-section views of exemplary embodiments), both in contrast to embodiments in which all of the spring arms extend downwardly or in which all of the spring arms extend upwardly (see, e.g., FIGS. 3.1 and 3.2 for side cross-section views of exemplary embodiments). These spider springs have two wide ends, each of which can be retained within a circular recess 102b of a plate 100b as shown in FIG. 5.5. The plates are rotatable relative to one another because the wide ends of the spider spring can rotate with respect to the plates having the circular recesses in which the wide ends seat (discussed above). Also, the plates are angulatable relative to one another because the spring arms of the spider spring can individually compress and restore, enabling one side of the spider spring to compress and restore as the plates angulate relative to one another, while other portions of the spider spring do not.

For another example, and referring to FIG. 5.6, the spider springs (e.g., spider springs 200d1–d2,h1–h2,l1–l2) that are designed to have the narrow end, with a ball-shaped protuberance (e.g., 206d1–d2,h1–h2,l1–l2), cooperate with a curvate socket 102d on an inwardly facing surface of a plate 100d also can cooperate with the spider springs (e.g., spider springs 200c1–c2,g1–g2,k1–k2) that are designed to have the narrow end, with a curvate socket (e.g., 206c1–c2,g1–g2, k1–k2), cooperate with a ball-shaped protuberance 102c on an inwardly facing surface of a plate 100c, so that the ball-shaped protuberance (e.g., 206d1–d2,h1–h2,l1–l2) of the one spider spring (e.g., 200d1–d2,h1–h2,l1–l2) freely rotates and angulates within the curvate socket (e.g., 206c1–c2,g1–g2,k1–k2) of the other spider spring (200c1–c2,g1–g2,k1–k2) through a range of angles. The structure of the curvate socket and the ball-shaped protuberance and the coupling of the ball-shaped protuberance with the curvate socket is as described above, and the wide ends of the combination spider spring are retained within a circular recess 102b of a respective cooperating plate 100b as shown in FIG. 5.6. The plates are rotatable relative to one another primarily because the ball-shaped protuberance rotates freely within the curvate socket, and secondarily because the wide ends of the spider springs can rotate with respect to the plates having the circular recesses in which the wide ends seat (discussed above). Also, the plates are angulatable relative to one another primarily because the ball-shaped protuberance angulates freely within the curvate socket, and secondarily because the spring arms of the spider springs can individually compress and restore, enabling one side of each spider spring to compress and restore as the plates angulate relative to one another, while other portions of the spider spring do not.

For another example, and referring to FIG. 5.7, similar to FIG. 5.2, in which a spider spring having a bored central hub (e.g., spider springs 200b1–b2,f1–f2,j1–j2) is rotatably secured to a flat surface on an inwardly facing surface of a plate by a flanged fastener (e.g., rivet, plug, dowel, or screw; rivet 115a is used herein as an example), the same type of spider spring can be rotatably secured to a narrow end of an opposing spider spring, the narrow end of the opposing spider spring having a flanged post. The flanged post, similar to the flanged rivet 115a of FIG. 5.2, has a flanged portion at the end of a post portion. The post portion has a diameter smaller than the diameter of the bore, and a length that is longer than the thickness of the bored spider spring's central hub, and the flanged portion has a diameter greater than the diameter of the bore. Thus, when the spider springs are coupled at their narrow ends so that the post portion passes through the bore and the flanged portion maintains the narrow end of the bored spider spring adjacent the narrow end of the opposing spider spring, the narrow ends are secured to one another so that they can still rotate with respect to one another. While any type of flanged post can be used within the scope of the invention, including but not limited to a threaded flanged post cooperating with a threaded bore at the narrow end of the opposing spider spring, FIG. 5.7 illustrates as one example a spider spring having a bored central hub (e.g., spider springs 200b1–b2,f1–f2,j1–j2) being rotatably secured in this fashion to a spider spring having a ball-shaped protuberance on its narrow end (e.g., spider springs 200d1–d2,h1–h2,l1–l2), wherein the ball-shaped protuberance (e.g., 206d1–d2, h1–h2,l1–l2) functions as the discussed flanged post. As noted above, the ball-shaped protuberance can radially compress to fit through the bore (e.g., 206b1–b2,f1–f2,j1–j2) to couple the spider springs to one another, and then a deflection preventing element (e.g., rivet, plug, dowel, or screw; rivets 224d1–d2,h1–h2,l1–l2 are used herein as examples) can be applied to the axial bore (e.g., 222d1–d2,h1–h2, l1–l2) of the ball-shaped protuberance to prevent the ball-shaped protuberance from thereafter radially compressing so that it cannot pass through the bore (e.g., 206b1–b2,f1–f2, j1–j2) again. The plates are rotatable relative to one another primarily because the coupling enable the narrow ends of the spider springs to rotate relative to one another, and secondarily because the wide ends of the spider springs can rotate with respect to the plates having the circular recesses in which the wide ends seat (discussed above). Also, the plates are angulatable relative to one another primarily because the spring arms of the spider springs can individually compress and restore, enabling one side of each spider spring to compress and restore as the plates angulate relative to one another, while other portions of the spider spring do not.

For another example, and referring to FIG. 5.8, some embodiments of the artificial disc of the invention can forego a spider spring altogether if axial compressibility is not desirable in a particular clinical application. More specifically, plates having a ball-shaped protuberance (e.g., plates of plate embodiment 100c) can cooperate with plates having a curvate socket (e.g., plates of plate embodiment 100d) so that the ball-shaped protuberance 102c of the one plate 100c freely rotates and angulates within the curvate socket 102d of the other plate 100d through a range of angles. The structure of the curvate socket and the ball-shaped protuberance and the coupling of the ball-shaped protuberance with the curvate socket is as described above. The plates are rotatable relative to one another because the ball-shaped protuberance rotates freely within the curvate socket, and angulatable relative to one another because the ball-shaped protuberance angulates freely within the curvate socket.

In embodiments having a ball-and-socket joint as described above, because the ball-shaped protuberance is held within the curvate socket by a rivet in the axial bore preventing radial compression of the ball-shaped protuberance, the artificial disc can withstand tension loading of the plates, as necessary for proper anatomical response. More particularly, when a tension load is applied to the plates, the ball-shaped protuberance in the curvate socket seeks to radially compress to fit through the opening of the curvate socket. However, the rivet in the axial bore of the ball-shaped protuberance prevents the radial compression, thereby preventing the ball-shaped protuberance from exiting the curvate socket. Further, in embodiments that have (additionally or alternatively) a spider spring, as the wide end of the spider spring seeks to escape the circular recess of the plate, the rivets holding the shield in place over the spider spring prevent the shield from separating from the plate when the spider spring presses against the inner surface of the shield. Further, in embodiments where the narrow end of the spider spring is secured against a plate or a narrow end of another spider spring by a rivet, rotatably or otherwise, the flanged portion of the rivet prevents the separation of the narrow end(s) of the spider spring(s). Therefore, the assembly does not come apart under normally experienced tension loads. This ensures that no individual parts of the assembly will pop out or slip out from between the vertebral bodies when the patient stretches or hangs while exercising or performing other activities. Thus, in combination with the securing of the plates to the adjacent vertebral bones via the mesh domes, the disc assembly has an integrity similar to the tension-bearing integrity of a healthy natural intervertebral disc.

Further, because the plates in some embodiments are made angulatable relative to one another by the ball-shaped protuberance being rotatably and angulatably coupled in a curvate socket, the disc assembly provides a centroid of motion within the ball-shaped protuberance. Accordingly, in those embodiments, the centroid of motion of the disc assembly remains centrally located between the vertebral bodies, similar to the centroid of motion in a healthy natural intervertebral disc.

While there has been described and illustrated specific embodiments of an artificial disc, it will be apparent to those skilled in the art that variations and modifications are possible without deviating from the broad spirit and principle of the invention. The invention, therefore, shall not be limited to the specific embodiments discussed herein.

What is claimed is:

1. An intervertebral spacer device, comprising: first and second plates, said plates being disposed in a spaced apart relationship such that a plate surface of said first plate faces a plate surface of said second plate, said facing surfaces being inner surfaces, and alternative faces of each plate being outer surfaces; and at least one restoring force providing element disposed between the inner surfaces of said first and second plates, and disposed such that a compressive load applied to the outer surfaces of said first and second plates is counteracted by said at least one restoring force providing element, said at least one restoring force providing element including at least one spider spring having a central hub and a plurality of spring arms extending radially from the central hub, wherein one of said first plate and said at least one spider spring comprises a curvate socket and the other of said first plate and said at least one spider spring comprises a semispherical protuberance that is rotatably and angulatably couplable to the curvate socket, wherein the semispherical protrusion comprises a radially deflectable semispherical portion and the curvate socket has an interior volume and an opening leading to the interior volume, the curvate socket accommodating the semispherical portion for free rotation and angulation therein, the semispherical portion fitting through the opening only when radially deflected, the semispherical portion being adapted to receive a deflection preventing element that when applied to the semispherical portion prevents the semispherical portion from fitting through the opening, wherein the semispherical protuberance comprises at least one radial slot such that the semispherical protuberance is radially deflectable upon the application of a radially inwardly directed force.

2. The intervertebral spacer device of claim 1, wherein the semispherical protuberance further comprises an axial bore into which a deflection preventing element is disposable to prevent the radial deflection of the semispherical protuberance.

3. An intervertebral spacer device, comprising: first and second plates, said plates being disposed in a spaced apart relationship such that a plate surface of said first plate faces a plate surface of said second plate, said facing surfaces being inner surfaces, and alternative faces of each plate being outer surfaces; and at least one restoring force providing element disposed between the inner surfaces of said first and second plates, and disposed such that a compressive load applied to the outer surfaces of said first and second plates is counteracted by said at least one restoring force providing element, said at least one restoring force providing element including at least one spider spring having a central hub and a plurality of spring arms extending radially from the central hub, wherein at least one of said first and second plates comprises a circular recess within which an end of the at least one spider spring is disposed, said spacer device further comprising a retaining element fastened to the at least one of said first and second plates having the circular recess, the retaining element preventing the dislocation of the end of the at least one spider spring from the circular recess.

4. An intervertebral spacer device, comprising: first and second plates, said plates being disposed in a spaced apart relationship such that a plate surface of said first plate faces a plate surface of said second plate, said facing surfaces being inner surfaces, and alternative faces of each plate being outer surfaces; and at least one restoring force providing element disposed between the inner surfaces of said first and second plates, and disposed such that a compressive load applied to the outer surfaces of said first and second plates is counteracted by said at least one restoring force providing element, said at least one restoring force providing element including at least one spider spring having a central hub and a plurality of spring arms extending radially from the central hub, wherein at least one of said first and second plates comprises on its outer surface an element that is deformably reshapeable under anatomical loads to securably engage a vertebral body endplate.

5. An intervertebral spacer device, comprising: first and second plates, said plates being disposed in a spaced apart relationship such that a plate surface of said first plate faces a plate surface of said second plate, said facing surfaces being inner surfaces, and alternative faces of each plate being outer surfaces; and at least one restoring force providing element disposed between the inner surfaces of said first and second plates, and disposed such that a compressive load applied to the outer surfaces of said first and second plates is counteracted by said at least one restoring force providing element, said at least one restoring force providing element including at least one spider spring having a central hub and a plurality of spring arms extending radially from the central hub, wherein at least one of spring arms is selected from the group consisting of a spring arm having parallel arm sides and a spring arm having diverging arm sides, wherein each spring arm has at least one radially extending groove.

* * * * *